United States Patent
George et al.

(10) Patent No.: US 10,870,613 B2
(45) Date of Patent: *Dec. 22, 2020

(54) PROCESS FOR THE PREPARATION OF 2,3,3,3-TETRAFLUOROPROPENE

(71) Applicant: SRF Limited, Gurgaon (IN)

(72) Inventors: Jose George, Gurgaon (IN); Sunil Raj, Gurgaon (IN); Ambuj Mishra, Gurgaon (IN); Anurag Katiyar, Gurgaon (IN); Rajdeep Anand, Gurgaon (IN)

(73) Assignee: SRF Limited, Gurgaon (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/464,901

(22) PCT Filed: Nov. 24, 2017

(86) PCT No.: PCT/IN2017/050555
§ 371 (c)(1),
(2) Date: May 29, 2019

(87) PCT Pub. No.: WO2018/100586
PCT Pub. Date: Jun. 7, 2018

(65) Prior Publication Data
US 2020/0010390 A1   Jan. 9, 2020

(30) Foreign Application Priority Data

Nov. 29, 2016  (IN) .............................. 201611040763
Jul. 7, 2017    (IN) .............................. 201711023883

(51) Int. Cl.
*C07C 17/278*  (2006.01)
*C07C 21/18*   (2006.01)

(52) U.S. Cl.
CPC ............ *C07C 17/278* (2013.01); *C07C 21/18* (2013.01)

(58) Field of Classification Search
CPC ... C07C 17/269; C07C 17/278; C07C 17/383; C07C 21/18; C07C 17/389
See application file for complete search history.

(56) References Cited

U.S. PATENT DOCUMENTS

| | | | |
|---|---|---|---|
| 2,931,840 A | 4/1960 | Marquis | |
| 10,239,804 B2 * | 3/2019 | George | C07C 17/269 |
| 2015/0005538 A1 * | 1/2015 | Furuta | C07C 17/269 |
| | | | 570/159 |
| 2016/0347692 A1 * | 12/2016 | Tirtowidjojo | C07C 17/269 |

FOREIGN PATENT DOCUMENTS

| | | |
|---|---|---|
| EP | 2826766 A1 | 1/2015 |
| JP | 2016027004 A | 2/2016 |
| WO | 2014080916 A1 | 5/2014 |

OTHER PUBLICATIONS

International Search Report and Written Opinion pertaining to PCT/IN2017/050555 dated Jan. 30, 2018.

* cited by examiner

*Primary Examiner* — Jafar F Parsa
(74) *Attorney, Agent, or Firm* — Dinsmore & Shohl, LLP

(57) ABSTRACT

The present invention provides an improved process for preparation of 2,3,3,3-tetrafluoropropene, wherein recyclization of the reaction by-products result in equilibrium between feed and outlet composition.

6 Claims, 3 Drawing Sheets

PROCESS FOR THE PREPARATION OF 2,3,3,3-TETRAFLUOROPROPENE

FIELD OF THE INVENTION

Figure 1:
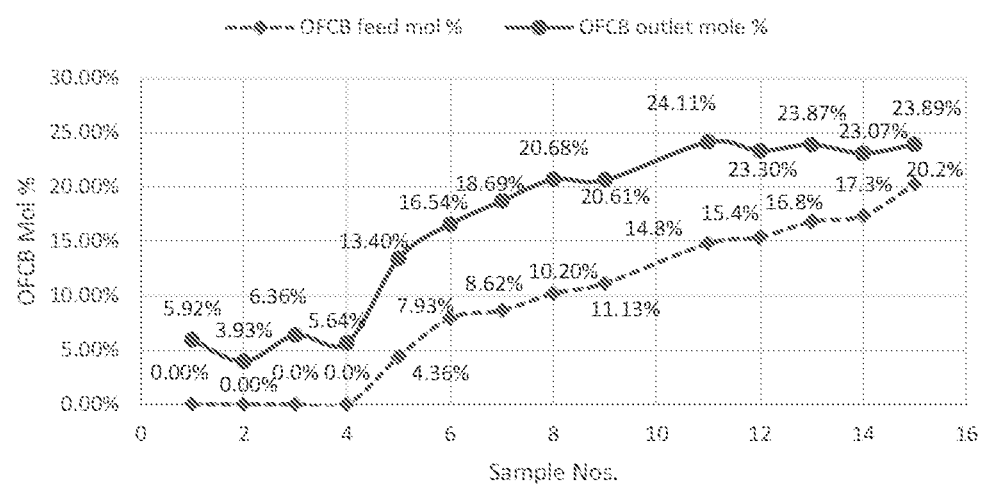

The present invention provides an improved process for the preparation of 2,3,3,3-tetrafluoropropene by recycling the reaction by-products and attaining an equilibrium between feed and outlet composition.

BACKGROUND OF THE INVENTION

Fluoro olefins play an important role as refrigerants. In recent years a fluoro olefin viz. 2,3,3,3-tetrafluoropropene (HFO-1234yf) has attracted attention as a new refrigerant to replace another fluorinated refrigerants namely 1,1,1,2-tetrafluoroethane (HFC-134a).

U.S. Pat. No. 2,931,840 describes a process for the preparation of HFO-1234yf by heating and decomposing a mixture of methyl chloride and chlorodifluoromethane or tetrafluoroethylene at a temperature from 700 to 950° C. by a common heating means such as an electric heater in a reactor.

It has been observed that the said process results in low yield due to formation of several by-products. It does not disclose any method for recycling the by-products.

Japan Publication No. 2016-027004 describes a process for the preparation of HFO-1234yf by feeding heat source selected from steam, nitrogen or carbon dioxide into a reactor containing a mixture of methyl chloride and tetrafluoroethylene at a temperature from 400 to 870° C. It further discloses recycling of vinylidenefluoride (VDF), hexafluoropropene (HFP), and chlorotrifluoroethylene (CTFE), which are used as raw materials for preparing HFO-1234yf, however, it discloses nothing about equilibrium between feed and outlet composition. Surprisingly, the present inventors observed that recycling of the composition comprising vinylidenefluoride (VDF), hexafluoropropene (HFP), octafluorocyclobutane (OFCB), 1-chloro-1,1,2,2,3,3-hexafluoropropane (R-226cb), chlorotetrafluoroethane (R-124), difluoromethane and trifluoromethane back into the reactor reduces further formation of these compounds by attaining an equilibrium, thereby increasing the yield of 2,3,3,3-tetrafluoropropene.

The present inventors have observed that upon feeding methylchloride and tetrafluoroethylene, pre-mixed or separately, into pre-heated reactor at 300° C. to 700° C. results in the formation of 2,3,3,3-tetrafluoropropene at high rate as compared to feeding heat source selected from steam, nitrogen or carbon dioxide into a reactor containing a mixture of methylchloride and tetrafluoroethylene at a similar temperature range.

The present inventors have further observed that feeding methylchloride and tetrafluoroethylene, pre-mixed or separately, into pre-heated reactor at 300° C. to 700° C. in the presence of initiator results in better selectivity towards 2,3,3,3-tetrafluoropropene. This was primarily because the content of methane (R50) reduces drastically upon the use of aforementioned initiators.

OBJECT OF THE INVENTION

A first object of the present invention provides an improved process for the preparation of 2,3,3,3-tetrafluoropropene comprising an initiator.

Another object of the present invention provides an improved process for the preparation of 2,3,3,3-tetrafluoropropene, wherein recyclization of the reaction by-products result in equilibrium between feed and outlet composition.

SUMMARY OF THE INVENTION

A first aspect of the present invention provides an improved process for the preparation of 2,3,3,3-tetrafluoropropene comprising:
  a) providing the heat source in the reactor;
  b) providing preheated methyl chloride, tetrafluoroethylene and an initiator, either pre-mixed or added separately, in the reactor to obtain the first reaction mixture;
  c) heating the first reaction mixture using heat source to obtain 2,3,3,3-tetrafluoropropene and second reaction mixture components;
  d) recycling the second reaction mixture components into the reactor to attain an equilibrium; and
  e) isolating 2,3,3,3-tetrafluoropropene.

A second aspect of the present invention provides a process for the preparation of 2,3,3,3-tetrafluoropropene comprising:
  a) providing a heat source in a reactor;
  b) providing methylchloride and tetrafluoroethylene, pre-mixed or added separately, in the reactor to obtain a mixture;
  c) contacting step b) mixture with heat source to obtain a reaction mixture comprising 2,3,3,3-tetrafluoropropene; and
  d) isolating 2,3,3,3-tetrafluoropropene from step c).

A third aspect of the present invention provides a process for the preparation of 2,3,3,3-tetrafluoropropene comprising:
  a) providing a heat source in a reactor;
  b) providing methylchloride and tetrafluoroethylene, said mixture is either premixed or added separately, in the reactor to obtain a mixture;
  c) contacting the step b) mixture with heat source in the presence of initiator to obtain a reaction mixture comprising 2,3,3,3-tetrafluoropropene; and
  d) isolating 2,3,3,3-tetrafluoropropene from step c).

A fourth aspect of the present invention provides a process for the preparation of 2,3,3,3-tetrafluoropropene comprising:
  a) providing methylchloride, tetrafluoroethylene and initiator, said mixture is either premixed or added separately, in the reactor to obtain a mixture;
  b) providing the heat source in the reactor;
  c) contacting the heat source and the step a) mixture to obtain a reaction mixture comprising 2,3,3,3-tetrafluoropropene; and
  d) isolating 2,3,3,3-tetrafluoropropene from step c).

A fifth aspect of the present invention provides a process for the preparation of 2,3,3,3-tetrafluoropropene comprising:
  a) providing a heat source in a reactor;
  b) providing methylchloride, tetrafluoroethylene and initiator, said mixture is either premixed or added separately, in the reactor to obtain a mixture;
  c) contacting step b) mixture with heat source to obtain a reaction mixture comprising 2,3,3,3-tetrafluoropropene; and
  d) isolating 2,3,3,3-tetrafluoropropene from step c).

BRIEF DESCRIPTION OF THE INVENTION

FIG. 1: The graph, it is evident that initially as the concentration of OFCB in reactor inlet increases, the concentration of OFCB in reactor outlet also increases but after a certain level, further increase in OFCB concentration in reactor outlet stops with the increase in OFCB concentration in reactor inlet. Thus an equilibrium was said to be attained.

Figure 2:
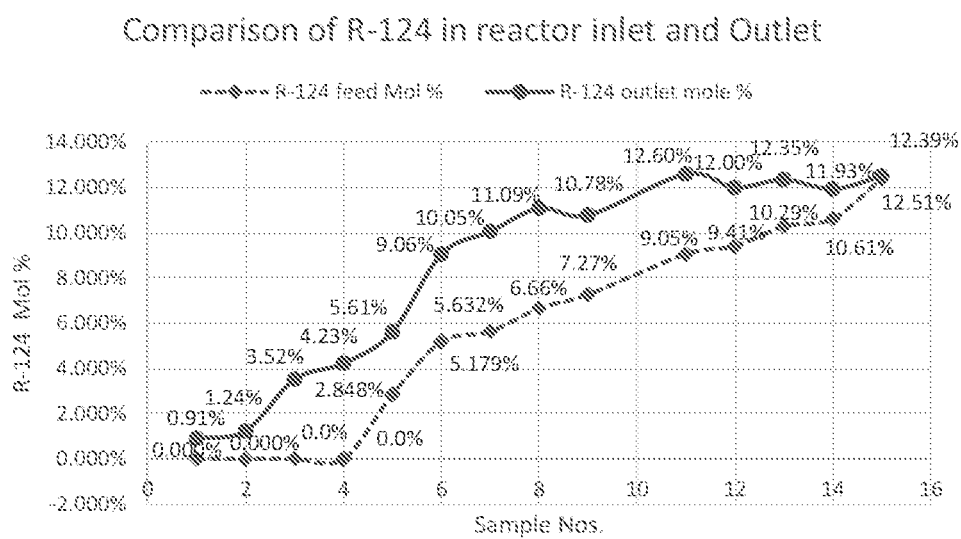

FIG. 2: The graph, it is evident that initially as the concentration of R-124 in reactor inlet increases, the concentration of R-124 in reactor outlet also increases but after a certain level, further increase in R-124 concentration in reactor outlet stops with the increase in R-124 concentration in reactor inlet. Thus an equilibrium was said to be attained.

Figure 3:
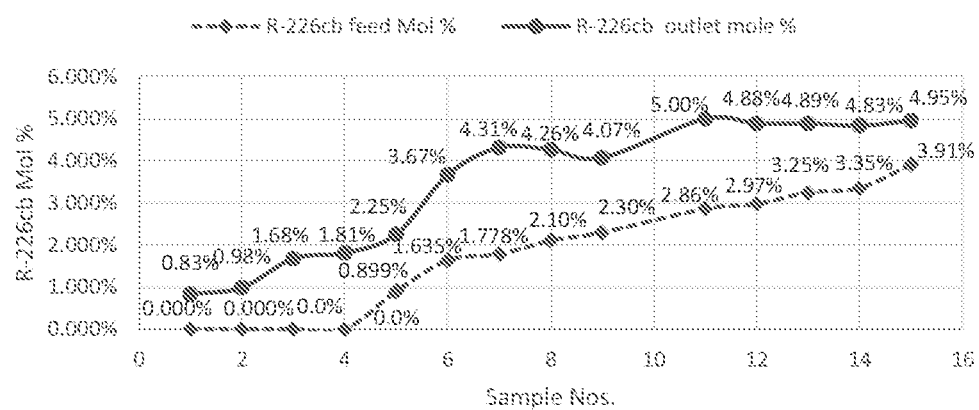

FIG. 3: From the above graph, it is evident that initially as the concentration of R-226cb in reactor inlet increases, the concentration of R-226cb in reactor outlet also increases but after a certain level further increase in R-226cb concentration in reactor outlet stops with the increase in R-226cb concentration in reactor inlet. Thus an equilibrium was said to be attained.

DETAILED DESCRIPTION OF THE INVENTION

A first aspect of the present invention provides an improved process for the preparation of 2,3,3,3-tetrafluoropropene comprising:
 a) providing the heat source in the reactor;
 b) providing preheated methyl chloride, tetrafluoroethylene and an initiator, either pre-mixed or added separately, in the reactor to obtain the first reaction mixture;
 c) heating the first reaction mixture using heat source to obtain 2,3,3,3-tetrafluoropropene and second reaction mixture components;
 d) recycling the second reaction mixture components into the reactor to attain an equilibrium; and
 e) isolating 2,3,3,3-tetrafluoropropene.

The heat source provided in the reactor is electric furnace or electrical heater.

The methyl chloride, tetrafluoroethylene and an initiator used in the step b) are preheated at 250° C. to 400° C. using the electric furnace and are continuously introduced into the reactor either premixed or separately and first reaction mixture is obtained. The second reaction mixture component obtained in step c) comprises vinylidenefluoride, chlorotetra fluoroethane, hexafluoropropene, octafluorocyclobutane, chlorodifluoromethane, 1-chloro-2,2-difluoroethene, 1,1,2,2,3,3-hexafluoropropane, 1-chloro-1,1,2,2,3,3-hexafluoropropane, difluoromethane and trifluoromethane.

The present invention of first aspect is carried out in continuous reaction mode wherein reaction by-products are recycled back into the reactor.

The reaction by-products comprise second reaction mixture components.

Initially as the concentration of second reaction mixture components in reactor inlet increased, the concentration of second reaction mixture components in reactor outlet also increased however after a certain level further increase in second reaction mixture components in reactor outlet stopped with the increase in second reaction mixture components in reactor inlet, thereby attaining an equilibrium between feed and outlet of the reactor.

The recycling of the second reaction mixture back into the step b) reactor also resulted in controlling the heat generated during reaction, thereby controlling reaction exothermicity which reduced the further formation of second reaction mixture components and resulted in increasing the yield of 2,3,3,3-tetrafluoropropene.

A second aspect of the present invention provides a process for the preparation of 2,3,3,3-tetrafluoropropene comprising:
 a) providing a heat source in a reactor;
 b) providing methylchloride and tetrafluoroethylene, premixed or added separately, in the reactor to obtain a mixture;
 c) contacting step b) mixture with heat source to obtain a reaction mixture comprising 2,3,3,3-tetrafluoropropene; and
 d) isolating 2,3,3,3-tetrafluoropropene from step c).

A third aspect of the present invention provides a process for the preparation of 2,3,3,3-tetrafluoropropene comprising:
 a) providing a heat source in a reactor;
 b) providing methylchloride and tetrafluoroethylene, said mixture is either premixed or added separately, in the reactor to obtain a mixture;
 c) contacting the step b) mixture with heat source in the presence of initiator to obtain a reaction mixture comprising 2,3,3,3-tetrafluoropropene; and
 d) isolating 2,3,3,3-tetrafluoropropene from step c).

A fourth aspect of the present invention provides a process for the preparation of 2,3,3,3-tetrafluoropropene comprising:
 a) providing methylchloride, tetrafluoroethylene and initiator, said mixture is either premixed or added separately, in the reactor to obtain a mixture;
 b) providing the heat source in the reactor;
 c) contacting the heat source and the step a) mixture to obtain a reaction mixture comprising 2,3,3,3-tetrafluoropropene; and
 d) isolating 2,3,3,3-tetrafluoropropene from step c).

A fifth aspect of the present invention provides a process for the preparation of 2,3,3,3-tetrafluoropropene comprising:
 a) providing a heat source in a reactor;
 b) providing methylchloride, tetrafluoroethylene and initiator, said mixture is either premixed or added separately, in the reactor to obtain a mixture;
 c) contacting step b) mixture with heat source to obtain a reaction mixture comprising 2,3,3,3-tetrafluoropropene; and
 d) isolating 2,3,3,3-tetrafluoropropene from step c).

The heat source provided in the reactor is electric furnace/electrical heater. Further, the heat source is used to provide a temperature in range of 250° C. to 700° C. or used to provide a temperature to a mixture of methylchloride and tetrafluoroethylene in the range of 250° C. to 700° C. in the reactor, or both to obtain a mixture.

In preferred embodiment the methylchloride is continuously introduced in the electric furnace set at the furnace temperature of 250° C. to 300° C., and methylchloride (R40) is heated at 300° C. The tetrafluoroethylene is continuously introduced into the tube in the electric furnace set at the furnace temperature of 300° C., and tetrafluoroethylene is preheated at 300° C. The initiator is continuously introduced into the tube in the electric furnace set at the furnace temperature of 300° C., and initiator is preheated at 300° C. These preheated material gas components (methylchloride, tetrafluoroethylene and initiator) are supplied to the reactor managed by the internal temperature.

The initiator used in the present inventions is selected from the group consisting of carbon tetrachloride, hexachloroethane, trichloroacetylchloride, chloroform, phosgene, thionyl chloride, sulfonyl chloride, trichloromethylbenzene, organic hypochlorites and inorganic hypochlorites or mixture thereof.

The concentration of initiator with respect to methyl chloride is selected from 0.1 to 8%. The mole ratio of methyl chloride to tetrafluoroethyelene is selected from 0.1 to 3:1.

The reaction mixture comprising 2,3,3,3-tetrafluoropropene, obtained by the present invention, is optionally, converted to anhydrous reaction mixture comprising 2,3,3,3-tetrafluoropropene.

In the present invention the above processes for the preparation of 2,3,3,3-tetrafluoropropene are optionally carried out in the presence of an inert gas selected from argon and nitrogen.

The isolation of 2,3,3,3-tetrafluoropropene, obtained by present invention, is carried out using several techniques known in the prior art such as distillation, adsorption, absorption and a like or combination thereof.

The residence time of the raw materials in the reaction zone is 0.1 second to 3.5 seconds.

The following examples are given by way of illustration and therefore should not be construed to limit the scope of the present invention.

EXAMPLES

Example 1: Process for the Preparation of 2,3,3,3-tetrafluoropropene

A mixture of tetrafluoroethylene and methylchloride in the molar ratio of 1:0.82 respectively is preheated and then superheated to 350° C. and was fed to the Inconel reactor which pre-heated and maintained at 620° C. by electrical heater.

Comparative results of with and without initiator on the yield of 2,3,3,3-tetrafluoropropene:

| | | |
|---|---|---|
| Initiator % (carbon tetrachloride) by mass of methylchloride | 0 | 1.3% |
| Temperature (° C.) | 620 | 620 |
| Tetrafluoroethylene:methyl chloride (molar ratio) | 1:0.82 | 1:0.83 |
| Residence time (Seconds) | 2.74 | 0.86 |
| Initiator % (carbon tetrachloride) | 0 | 1.3% |
| Composition | | |
| methane | 13.17% | 0.49% |
| tetrafluoroethylene | 20.16% | 9.90% |
| trifluoromethane | 0.25% | 1.07% |
| vinylidenefluoride | 1.63% | 2.23% |
| trifluoroethyelene | 0.16% | 0.30% |
| difluoromethane | 1.06% | 0.09% |
| Hexafluoropropene | 1.14% | 12.72% |
| chlorodifluoromethane | 4.13% | 2.15% |
| 2,3,3,3-tetrafluoropropene | 3.95% | 15.62% |
| octafluorocyclobutane | 6.49% | 6.96% |
| chlorofluoroethyelenes | 3.21% | 4.20% |
| methylchloride | 33.64% | 25.93% |
| chlorofluoroethanes | 0.86% | 3.19% |
| chlorofluoropropenes | 5.48% | 1.83% |
| chlorofluoropropanes | 2.00% | 2.01% |
| Total tetrafluoroethyelene conversion | 60% | 85% |
| 2,3,3,3-tetrafluoropropene Selectivity | 12% | 25.5% |
| Formation of methane in comparison to formation of 2,3,3,3-tetrafluoropropene | 333% | 3.13% |
| Formation of vinylidenefluoride in comparison to formation of 2,3,3,3-tetrafluoropropene | 41.2% | 14.2% |
| Formation of octafluorocyclobutane in comparison to formation of 2,3,3,3-tetrafluoropropene | 164.3% | 44.5% |

Example 2: Process for the Preparation of 2,3,3,3-tetrafluoropropene

A mixture of tetrafluoroethylene and methylchloride in the mol ratio of 1:1.16 respectively is preheated and then superheated to 350° C. and was fed to the Inconel reactor which is maintained at 550° C. by electrical heater.

| | |
|---|---|
| Temperature | 550° C. |
| M.R (tetrafluoroethyelene:methylchloride) | 1:1.16 |
| Residence time (Seconds) | 3.19 |
| Initiator % (carbon tetrachloride) by mass of methylchloride | 5 |
| Composition | |
| methane | 0.02% |
| tetrafluoroethyelene | 20.44% |
| trifluoromethane | 0.06% |
| vinylidenefluoride | 0.77% |
| trifluoroethyelene | 0.06% |
| difluoromethane | 0.04% |
| hexafluoropropene | 3.10% |
| chlorotrifluoroethyelene | 0.07% |
| chlorodifluoromethane | 1.02% |
| 2,3,3,3-tetrafluoropropene | 11.89% |
| octafluorocyclobutane | 2.23% |
| chlorofluoroethyelenes | 8.78% |
| methylchloride | 36.02% |
| chlorofluoroethanes | 0.96% |
| chlorofluoropropenes | 3.0% |
| chlorofluoropropanes | 3.05% |
| tetrafluoroethyelene (TFE) Conversion | 62% |
| tetrafluoroethyelene (TFE) Selectivity | 28.5% |
| Formation of methane in comparison to formation of 2,3,3,3-tetrafluoropropene | 0.17% |
| Formation of vinylidenefluoride in comparison to formation of 2,3,3,3-tetrafluoropropene | 6.48% |
| Formation of Trifluoromethane in comparison to formation of 2,3,3,3-tetrafluoropropene | 0.50% |
| Formation of Difluoromethane in comparison to formation of 2,3,3,3-tetrafluoropropene | 0.34% |
| Formation of Octafluorocyclobutane in comparison to formation of 2,3,3,3-tetrafluoropropene | 18.75% |

Example 3: Process for the Preparation of 2,3,3,3-tetrafluoropropene

| | | |
|---|---|---|
| Temperature | 808° C. | 620° C. |
| M.R (tetrafluoroethyelene:methyl chloride) | 1:3 | 1:1.2 |
| Residence time (Seconds) | 2.19 | 2.53 |
| Composition | | |
| methane | 2.45% | 5.15% |
| tetrafluoroethyelene | 7.72% | 25.28% |
| trifluoromethane | 1.71% | 0.17% |
| vinylidenefluoride | 13.89% | 1.18% |
| trifluoroethyelene | 0.724% | 0.16% |
| difluoromethane | 1.05% | 0.47% |
| hexafluoropropene | 1.97% | 0.48% |
| chlorodifluoromethane | 1.35% | 3.25% |
| 2,3,3,3-tetrafluoropropene | 5.55% | 2.67% |
| octafluorocyclobutane | 0.67% | 9.11% |
| methylchloride | 59.52% | 46.52% |
| Formation of vinylidenefluoride in comparison to formation of 2,3,3,3-tetrafluoropropene | 250% | 44% |
| Formation of Trifluoromethane in comparison to formation of 2,3,3,3-tetrafluoropropene | 31% | 6.4% |
| Formation of Difluoromethane in comparison to formation of 2,3,3,3-tetrafluoropropene | 18.9% | 17.6% |

The isolation of 2,3,3,3-tetrafluoropropene from the reaction mixture/composition, obtained by the process of present invention, is carried out by any method known in the art, for example, by series of distillations, absorption and adsorption or mixture thereof.

Example 4: Preparation of 2,3,3,3-tetrafluoropropene by Attaining an Equilibrium by Recycling of vinylidenefluoride at 680° C.

A mixture of methyl chloride and tetrafluoroethylene in the mole ratio of 0.88 together with carbon tetrachloride was preheated and then superheated to 350° C. and was fed to the reactor which was maintained at 620° C. by electrical heater. The reaction was exothermic and the temperature increased to 680° C. The reaction mixture thus obtained consisted of HFO1234yf, VDF and other by-products. The VDF was recycled back into the reactor. The reactor outlet samples were analyzed initially and after recycling of VDF using a gas chromatograph equipped with thermal conductivity detector. The results are shown in Table-1.

TABLE 1

| | Reactor Inlet | | | |
|---|---|---|---|---|
| | Sample Number | | | |
| | 1 | 2 | 3 | 4 |
| Reaction temperature (° C.) | 680 | 680 | 680 | 680 |
| Pressure (Kg/cm2) | 1 | 1 | 1 | 1 |
| Mole Ratio (R40:TFE) | 0.8 | 0.8 | 0.8 | 0.8 |
| VDF Mole % | 0.0% | 14.1% | 28.1% | 27.9% |
| Reactor outlet (analysis in mole %) | | | | |
| Methane | 0.05% | 0.08% | 0.07% | 0.08% |
| Tetrafluoroethyelene | 2.58% | 3.38% | 3.70% | 3.51% |
| Trifluoromethane | 3.62% | 2.29% | 1.98% | 1.61% |
| Vinylidenefluoride | 12.96% | 15.69% | 18.27% | 16.30% |
| Difluoromethane | 1.31% | 1.58% | 1.49% | 1.40% |
| Hexafluoropropene | 5.71% | 6.01% | 6.62% | 6.80% |
| Trifluoroethene | 1.01% | 0.91% | 0.85% | 0.72% |
| Octafluorocyclobutane | 4.17% | 4.63% | 4.80% | 4.93% |
| 2,3,3,3-Tetrafluoropropene | 18.80% | 18.98% | 18.04% | 16.61% |
| Tetrafluoroethane | 1.15% | 1.25% | 1.24% | 1.16% |
| Chlorodifluoromethane | 5.30% | 4.64% | 4.45% | 4.08% |
| Methyl chloride | 2.04% | 5.17% | 5.93% | 7.15% |
| Chlorotetrafluoroethane | 3.39% | 1.59% | 1.36% | 1.20% |
| 1,1,2,2,3,3-Hexafluoropropane | 2.18% | 2.56% | 2.47% | 2.58% |
| 1-Chloro-2,2-difluoro ethylene | 7.47% | 6.27% | 5.90% | 5.64% |
| 1-Chloro-1,1,2,2,3,3-hexafluoropropane | 1.78% | 1.61% | 1.48% | 1.43% |
| 1,1-Dichloro-2,2-difluoro ethane | 3.62% | 1.97% | 1.79% | 1.73% |
| 1-Chloro-2,2,3,3-tetrafluoro propane | 0.93% | 1.97% | 2.02% | 2.54% |
| Based on TFE conversion, HFO-1234yf selectivity | 19.72% | 24.56% | 28.99% | 27.09% |

Example 5: Preparation of 2,3,3,3-tetrafluoropropene by Attaining an Equilibrium by Recycling of Vinylidenefluoride at 708° C.

A mixture of methyl chloride and tetrafluoroethylene in the mole ratio of 0.88 together with carbon tetrachloride was preheated and then superheated to 350° C. and was fed to the reactor which was maintained at 620° C. by electrical heater. The reaction was exothermic and the temperature increased to 708° C. The reaction mixture thus obtained consisted of HFO1234yf, VDF and other by-products. The VDF was recycled back into the reactor. The reactor outlet samples were analyzed initially and after recycling of VDF using a gas chromatograph equipped with thermal conductivity detector. The results are shown in Table-2.

TABLE 2

| | Reactor Inlet | | | |
|---|---|---|---|---|
| | Sample No. | | | |
| | 1 | 2 | 3 | 4 |
| Reactor Skin Temperature (° C.) | 620 | 620 | 620 | 620 |
| Temperature Process (° C.) | 708 | 708 | 708 | 708 |
| Pressure Kg/cm2 | 1 | 1 | 1 | 1 |
| Mole Ratio (R40:TFE) | 0.9 | 0.9 | 0.9 | 0.9 |
| VDF Mole % | 0.0% | 21.7% | 15.7% | 20.0% |
| Reactor outlet (analysis in mole %) | | | | |
| Methane | 0.21% | 0.11% | 0.13% | 0.08% |
| Tetrafluoroethyelene | 4.16% | 3.26% | 3.12% | 3.85% |
| Trifluoromethane | 2.70% | 2.30% | 1.87% | 1.91% |
| Vinylidenefluoride | 15.85% | 20.66% | 17.88% | 17.76% |
| Difluoromethane | 1.35% | 1.63% | 1.55% | 1.41% |
| Hexafluoropropene | 4.47% | 5.02% | 5.64% | 7.46% |
| Trifluoroethene | 0.98% | 0.79% | 0.65% | 0.76% |
| Octafluorocyclobutane | 4.11% | 2.93% | 3.22% | 3.96% |
| 2,3,3,3-Tetrafluoropropene | 19.88% | 19.57% | 18.30% | 18.31% |
| Tetrafluoroethane | 1.05% | 1.05% | 1.00% | 0.95% |
| Trifluoropropene | 0.25% | 0.28% | 0.25% | 0.22% |
| Chlorodufluoromethnae | 5.01% | 4.43% | 4.17% | 1.10% |
| Methyl chloride | 6.52% | 7.06% | 9.09% | 7.54% |
| Chlorotetrafluoroethane | 2.00% | 1.38% | 1.73% | 1.95% |
| 1,1,2,2,3,3-Hexafluoropropane | 2.12% | 1.82% | 1.94% | 1.91% |
| 1-Chloro-2,2-difluoroethylene | 6.98% | 6.06% | 5.65% | 5.57% |
| 1-Chloro-1,1,2,2,3,3-hexafluoropropane | 0.91% | 1.14% | 1.19% | 1.15% |
| 1,1-Dichloro-2,2-difluoroethene | 2.60% | 2.60% | 2.37% | 2.18% |
| Based on TFE conversion, R1234yf selectivity | 22.30% | 28.84% | 25.43% | 26.71% |

From the Tables-1 and Table-2, it is evident that initially as the concentration of VDF in reactor inlet increases, the concentration of VDF in reactor outlet also increases but after a certain level, further increase in VDF concentration in reactor outlet stops with the increase in VDF concentration in reactor inlet. Thus an equilibrium was said to be attained.

Example 6: Preparation of 2,3,3,3-tetrafluoropropene by Attaining an Equilibrium by Recycling OFCB, R-124 or R-226cb A mixture of methyl chloride and tetrafluoroethylene in the mole ratio of 0.88 was preheated and then superheated to 350° C. and was fed to the reactor which was maintained at 645° C. by electrical heater. The reaction was exothermic and the temperature increased to 680° C. The reaction mixture components thus obtained consisted of HFO-1234yf, octafluorocyclobutane (51.6 mole %), chlorotetrafluoroethane (33.4 mole %), 1-chloro-1,1,2,2,3,3-hexafluoropropane (9.8 mole %) and other by-products. The octafluorocyclobutane (51.6 mole %), chlorotetrafluoroethane (33.4 mole %), 1-chloro-1,1,2,2,3,3-hexafluoropropane (9.8 mole %) were recycled back into the reactor one by one. The reactor outlet samples were analyzed initially and after recycling of said reaction components using a gas chromatograph equipped with thermal conductivity detector. The results are shown in FIGS. 1,2 and 3.

The above experimental data clearly indicates that the presence of second reaction mixture components in reactor inlet results in an equilibrium which enhances the selectivity for the formation of 2,3,3,3-tetrafluoropropene.

However, this equilibrium is not limited to the compounds in the examples, it can be applied to most or all of the components of second reaction mixture.

We claim:

1. A process for preparation of 2,3,3,3-tetrafluoropropene consisting of:
   a) providing a heat source in a reactor;
   b) providing a mixture of methylchloride and tetrafluoroethylene, said mixture is either premixed or added separately, in the reactor to obtain a mixture;
   c) contacting the mixture with heat source in the presence of an initiator to obtain a reaction mixture comprising 2,3,3,3-tetrafluoropropene; and
   d) isolating 2,3,3,3-tetrafluoropropene,
   wherein, heat source is either an electric heater or a furnace,
   wherein, the initiator is selected from a group consisting of carbon tetrachloride, chloroform, or a mixture thereof.

2. The process of claim 1, wherein the initiator is added to the mixture of methylchloride and tetrafluoroethylene prior to contacting the mixture with the heat source.

3. The process of claim 1, wherein the initiator is added to the mixture of methylchloride and tetrafluoroethylene after contacting the mixture with the heat source.

4. The process of claim 1, wherein the reactor is a continuous or batch reactor.

5. The process of claim 1, wherein the mole ratio of methyl chloride to tetrafluoroethylene is selected from 0.1 to 3:1.

6. The process of claim 1, wherein the reactor is heated to a temperature in range of 250° C. to 700° C. or the reaction mixture is heated to a temperature in the range of 250° C. to 700° C. in the reactor, or both.

* * * * *